(12) United States Patent
Galopin et al.

(10) Patent No.: US 7,893,110 B2
(45) Date of Patent: *Feb. 22, 2011

(54) CARBOXYLIC ACID AMIDES PROVOKING A COOLING SENSATION

(75) Inventors: Christophe C. Galopin, Chesterfield, VA (US); Stefan Michael Furrer, Cincinnati, OH (US); Lori W. Tigani, Salisbury, MD (US); Jay Patrick Slack, Loveland, OH (US); Pablo Victor Krawec, Cincinnati, OH (US); Lucienne Cole, Cincinnati, OH (US)

(73) Assignee: Givaudan S.A., Vernier (CH)

( * ) Notice: Subject to any disclaimer, the term of this patent is extended or adjusted under 35 U.S.C. 154(b) by 337 days.

This patent is subject to a terminal disclaimer.

(21) Appl. No.: 11/884,497

(22) PCT Filed: Feb. 27, 2006

(86) PCT No.: PCT/CH2006/000119

§ 371 (c)(1),
(2), (4) Date: Dec. 19, 2007

(87) PCT Pub. No.: WO2006/092076

PCT Pub. Date: Sep. 8, 2006

(65) Prior Publication Data

US 2008/0176945 A1 Jul. 24, 2008

(30) Foreign Application Priority Data

Mar. 2, 2005 (GB) .................................. 0504194.2

(51) Int. Cl.
*A61K 31/165* (2006.01)
*C07C 255/58* (2006.01)
*C07C 233/00* (2006.01)
(52) U.S. Cl. ...................... 514/613; 558/404; 564/123
(58) Field of Classification Search ................. 514/613; 558/404; 564/123
See application file for complete search history.

(56) References Cited

U.S. PATENT DOCUMENTS

| 4,248,859 | A | 2/1981 | Rowsell et al. |
| 4,318,900 | A | 3/1982 | Rowsell et al. |
| 6,348,625 | B1 | 2/2002 | Anderson |
| 6,399,614 | B1* | 6/2002 | Leonardi et al. ........ 514/252.14 |
| 7,414,152 | B2* | 8/2008 | Galopin et al. .............. 564/189 |
| 2005/0084447 | A1* | 4/2005 | Wei ........................... 424/1.11 |
| 2005/0187211 | A1 | 8/2005 | Wei |
| 2006/0051301 | A1 | 3/2006 | Galopin et al. |
| 2006/0276667 | A1 | 12/2006 | Galopin et al. |

FOREIGN PATENT DOCUMENTS

| FR | 2 254 317 | 7/1975 |
| WO | WO-2006-056087 A1 | 6/2006 |

OTHER PUBLICATIONS

Datebase Cehmcats, Accession Nr. 2004:1396439; ChemBridge Screening Library, Order Nr. 5380996, Jan. 12, 2005, XP002384344, abstract.

* cited by examiner

*Primary Examiner*—Barbara P Badio
*Assistant Examiner*—Sara E Clark
(74) *Attorney, Agent, or Firm*—Curatolo Sidoti Co., LPA; Joseph G. Curatolo; Salvatore A. Sidoti

(57) ABSTRACT

The present invention refers to cooling compounds of formula I

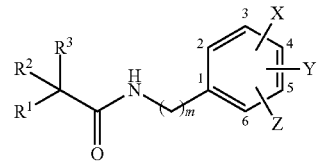

wherein R1, R2, R3, X, Y, Z, and m have the same meaning as given in the specification. The present invention refers furthermore to a process for their production and to product compositions comprising them.

2 Claims, No Drawings

CARBOXYLIC ACID AMIDES PROVOKING A COOLING SENSATION

CROSS REFERENCE TO RELATED APPLICATIONS

This application is a national stage application of International Application No. PCT/CH2006/000119, filed Feb. 27, 2006, which claims the benefit of Application No. GB 0504194.2, filed Mar. 2, 2005, from which applications priority is claimed, and which applications are incorporated herein by reference as if fully written out below.

The present invention refers to cooling compounds, namely compounds providing physiological cooling effects on the skin and on the mucous membranes of the mouth. The present invention refers furthermore to a process for their production and to product compositions comprising them.

In the flavor and fragrance industry there is an ongoing demand on compounds having unique cooling perception that provides the user with a pleasing cooling effect and which are well suitable in a variety of products, particularly in ingestible and topical products.

British Patent GB 1,421,744 reports the discovery of simple N-substituted amides having a physiological cooling effect. These chemicals are versatile because they can be made completely synthetically. Their starting material does not rely on a natural source, in contrast with N-substituted p-menthanecarboxamides described in U.S. Pat. No. 4,150,052.

Surprisingly it has been found that a certain class of carboxamides exhibits a strong cooling effect. Accordingly the invention refers in one of its aspects to the use of a compound of formula I as cooling agent

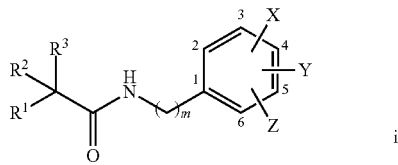

I wherein X is $(CH_2)_n$—R, wherein R is a group comprising at least one free electron pair and n is 0 or 1; and Y and Z are independently selected from the group consisting of H, OH, C1 to C4 alkyl, e.g. methyl, ethyl, iso-propy, and C1 to C4 alkoxy, e.g. methox and ethoxy; or X and Y form together a bivalent radical selected from the group consisting of —O—$CH_2$—O—, —N=CH—O— and —N=CH—S— forming together with the carbon atoms to which they are attached a 5-membered ring, i.e. a 1,3-dioxalane ring, 1,3-oxazole ring and 1,3-thiazole ring respectively; and Z is selected from the group consisting of H, OH, C1 to C4 alkyl, e.g. methyl, ethyl and iso-propyl, and C1 to C4 alkoxy, e.g. methoxy and ethoxy;

m is 0, 1, or 2;

$R^1$ is H, or C1 to C4 alkyl, preferably H or methyl; and $R^2$ and $R^3$ together with the carbon atom to which they are attached forms a 3 to 10, preferably 5 to 7, membered mono- or bicyclic carboxylic ring, e.g. cyclohexyl, cyclopentyl, bicyclo[2.2.1]heptyl, and bicyclo[2.2.1]heptenyl, optionally substituted by an alkyl residue having up to 4 carbon atoms, preferably 1 to 3 carbon atoms, e.g. tert-butyl, iso-propyl, methyl, and the ring may comprise one or more oxygen atoms, e.g. benzo[1,3]dioxolyl; with the proviso that $R^2$ and $R^3$ together with the carbon atom to which they are attached is not 2-isopropyl-5-methyl-cyclohexyl; or $R^1$, $R^2$ and $R^3$ together with the carbon atom to which they are attached forms a 6 to 10 membered tricyclic carboxylic ring, optionally substituted by an alkyl residue having up to 4 carbon atoms, preferably 1 to 3 carbon atoms, e.g. tert-butyl, iso-propyl, methyl, and the ring may comprise one or more oxygen atoms, preferably $R^1$, $R^2$ and $R^3$ together with the carbon atom to which they are attached is adamantyl.

The compounds of formula I may comprise several chiral centres and as such may exist as a mixture of stereoisomers, or they may be resolved as isomerically pure forms. Resolving stereoisomers adds to the complexity of manufacture and purification of these compounds and so it is preferred to use the compounds as mixtures of their stereoisomers simply for economic reasons. However, if it is desired to prepare individual stereoisomers, this may be achieved according to methods known in the art, e.g. preparative HPLC and GC, crystallization or stereoselective synthesis.

Particularly preferred compounds of formula I are those wherein X is in 2, 4 or 6-position for monocyclic compounds, namely for compounds of formula I wherein $R^2$ and $R^3$ form together with the carbon atom to which they are attached a monocyclic ring. The most preferred compounds are when X is in 2, 4 or 6-position and Y and Z independently represent hydrogen, hydroxyl, methoxyl or methyl.

Also preferred are compounds of formula I wherein X is in 3 or 5-position for bi- and tricyclic compounds, namely for compounds of formula I wherein $R^2$ and $R^3$ form together with the carbon atom to which they are attached a bicyclic carboxylic ring and compounds of formula I wherein $R^1$, $R^2$ and $R^3$ together with the carbon atom to which they are attached forms tricyclic carboxylic ring.

Particular preferred compounds of formula I are selected from the group consisting of 1-methyl-cyclohexanecarboxylic acid (3-methoxy-phenyl)-amide (Ex. 1), 1-methyl-cyclohexane-carboxylic acid (4-cyano-phenyl)-amide (Ex. 2A), 2-methyl-bicyclo[2.2.1]hept-5-ene-2-carboxylic acid (4-cyano-phenyl)-amide (Ex. 2B), 2-methyl-bicyclo[2.2.1]hept-5-ene-2-carboxylic acid (4-methoxy-phenyl)-amide (Ex. 2C), 3-isopropyl-1-methyl-cyclopentanecarboxylic acid (4-methoxy-phenyl)-amide (Ex. 2D), 3-isopropyl-1-methyl-cyclopentanecarboxylic acid (3-cyano-phenyl)-amide (Ex. 2E), adamantane-1-carboxylic acid (4-methoxy-phenyl)-amide (Ex. 2F), adamantane-1-carboxylic acid (4-methoxy-phenyl)-amide*, adamantane-1-carboxylic acid (3-nitrophenyl)-amide*, 2-tert-butyl-cyclopentanecarboxylic acid (4-methoxy-phenyl)-amide (Ex. 2G), 2-tert-butyl-cyclohexanecarboxylic acid (2-methoxy-phenyl)-amide (Ex. 2H), 2-tert-butyl-cyclopentanecarboxylic acid (4-hydroxymethyl-phenyl)-amide (Ex. 2I), 2-tert-butyl-cyclopentanecarboxylic acid (4-acetyl-phenyl)-amide (Ex. 2J), 2-tert-butyl-cyclopentanecarboxylic acid (4-cyano-phenyl)-amide (Ex. 2K), 2-tert-butyl-cyclohexanecarboxylic acid (4-hydroxymethyl-phenyl)-amide (Ex. 2L), 2-tert-butyl-cyclohexanecarboxylic acid (4-acetyl-phenyl)-amide (Ex. 2M), and 2-tert-butyl-cyclohexane-carboxylic acid (4-cyano-phenyl)-amide (Ex. 2N).

*: commercially available from Sigma-Aldrich

Whereas some compounds have been described in the literature, others have not, and are novel. Thus, in an other aspect of the invention there is provided a compound of formula Ia

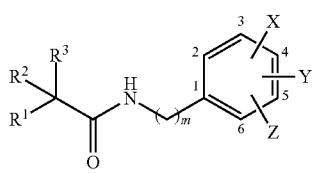

wherein X is $(CH_2)_n$—R, wherein R is a group comprising at least one free electron pair and n is 0 or 1; and Y and Z are independently selected from the group consisting of H, OH, C1 to C4 alkyl, e.g. methyl, ethyl and iso-propyl, and C1 to C4 alkoxy such as methoxy and ethoxy; or X and Y form together a bivalent radical selected from the group consisting of —O—$CH_2$—O—, —N=CH—O— and —N=CH—S— forming together with the carbon atoms to which they are attached a 5-membered ring, i.e. a 1,3-dioxalane ring, 1,3-oxazole ring and 1,3-thiazole ring respectively; and Z is selected from the group consisting of H, OH, C1 to C4 alkyl such as methyl, ethyl and iso-propyl, and C1 to C4 alkoxy such as methoxy and ethoxy;

m is 0, 1, or 2;

$R^1$ is H, or C1 to C4 alkyl, preferably H or methyl; and $R^2$ and $R^3$ together with the carbon atom to which they are attached forms a 3 to 10, preferably 5 to 7, membered mono- or bicyclic carboxylic ring, e.g. cyclohexyl, cyclopentyl, bicyclo[2.2.1]heptyl, and bicyclo[2.2.1]heptenyl, optionally substituted by an alkyl residue having up to 4 carbon atoms, preferably 1 to 3 carbon atoms, e.g. tert-butyl, iso-propyl, methyl, and the ring may comprise one or more oxygen atoms, e.g. benzo[1,3]dioxolyl; with the proviso that $R^2$ and $R^3$ together with the carbon atom to which they are attached is not 2-isopropyl-5-methyl-cyclohexyl.

Groups comprising at least one free electron pair are preferably selected from the group consisting of halogens, e.g. Cl, F, and Br, cyano, hydroxyl, methoxyl, ethoxyl, $NO_2$, acetyl, $SO_2NH_2$, CHO, COOH, C1 to C4 alkyl carboxylate such as $COOC_2H_5$ and $COOCH_3$, carboxamide of the formula C(O)NH—R', wherein R' is hydrogen, methyl, ethyl, propyl, iso-propyl, tert. propyl, n-butyl, tert. butyl or iso-butyl, and heterocyclic ring systems, preferably selected from the group consisting of 5- and 6-membered heterocyclic ring systems such as oxazole, triazole, pyrazole, and morpholine.

The compounds of formula I may be used in products that are applied to the mouth or the skin to give a cooling sensation. By "applying" is meant any form of bringing into contact, for example, oral ingestion or, in the case of tobacco products, inhalation. In the case of application to the skin, it may be, for example, by including the compound in a cream or salve, or in a sprayable composition. The invention therefore also provides a method of providing a cooling effect to the mouth or skin by applying thereto a product comprising a compound as hereinabove described.

Products that are applied to the mouth may include foodstuffs and beverages taken into the mouth and swallowed, and products taken for reasons other than their nutritional value, e.g. tablets, mouthwash, throat sprays, dentifrice and chewing gum. Products that are applied to the skin may be selected from perfumes, toiletries, lotions, oils and ointment applicable to the skin of the human body, whether for medical or other reasons. Accordingly, the present invention refers in a further aspect to a composition comprising an amount of a compound of formula I, or a mixture thereof, sufficient to stimulate the cold receptors in the areas of the skin or mucous membrane with which the composition comes into contact and thereby promote the desired cooling effect. A cooling effect may be achieved upon application of a liquid product to the mucous membrane, e.g. mouth mucous membrane, comprising less than 5000 ppm, preferably between 300 and 3000 ppm, of a compound of formula I.

Thus the present invention further relates to an end product selected from the group consisting of topical products, oral care products, nasal care products, toilet articles, ingestible products and chewing gum, which comprises a product base and an effective amount of a cooling compound of formula I, or a mixture thereof.

The compounds of the invention may be used alone or in combination with other cooling compounds known in the art, e.g. menthol, menthone, isopulegol. N-ethyl p-menthanecarboxamide (WS-3), N.2,3-trimethyl-2-isopropylbutanamide (WS-23), menthyl lactate, mono-menthyl succinate (PHYSCOOL®), mono-menthyl glutarate, O-menthyl glycerine (COOLACT® 10) and 2-sec-butylcyclohexanone (FRESKOMENTHE®).

The compounds of formula I may be prepared by chlorination of an acid of the general formula $R^1R^2R^3C$—COOH to the corresponding acid chloride which is further reacted with an amine of formula II

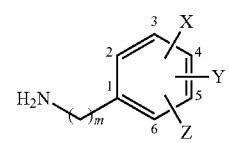

wherein $R^1$, $R^2$, and $R^3$, m, X, Y and Z have the same meaning as given for the compounds of formula I, under process conditions well known in the art. Certain acids of the formula $R^1R^2R^3C$—COOH are commercially available. In general they may be prepared for example by a method described in *Tetrahedron*, 1980, 36(6), 775-7 or *Journal of Chemical Research*, 1978, 2, 46.

The invention is now further described by means of the following non-limiting examples.

EXAMPLE 1

1-Methyl-cyclohexanecarboxylic Acid (3-methoxy-phenyl)-amide

To a flask were added 5.9 g (50 mmol) of 4-aminobenzonitrile, 4 mL of pyridine and 100 mL MtBE. To this mixture, 8 g of 1-methylcyclohexanecarboxyl chloride were added dropwise over 5 minutes. The reaction mixture was stirred for 24 h. To the reaction mixture, 50 mL of water were added. The mixture was separated. The organic layer was washed with 50 mL of water and 50 mL of brine. The organic layer was dried over MgSO$_4$. The solvent was evaporated *in vacuo* to afford the crude product, which was chromatographed over silica gel to afford 8.3 g of 1-methyl-cyclohexanecarboxylic acid (3-methoxy-phenyl)-amide.

MS: 242, 118, 97, 55

EXAMPLE 2

Following the same procedure according to Example 1 the compounds listed in Table 1 have been synthesised.

TABLE 1

| No. | Name | physical data |
|---|---|---|
| A | 1-Methyl-cyclohexanecarboxylic acid (4-cyano-phenyl)-amide | MS: 247, 123, 97, 55 |
| B | 2-Methyl-bicyclo[2.2.1]hept-5-ene-2-carboxylic acid (4-cyano-phenyl)-amide | MS: 252, 187, 107, 69 |
| C | 2-Methyl-bicyclo[2.2.1]hept-5-ene-2-carboxylic acid (4-methoxy-phenyl)-amide | MS: 252, 192, 191, 107, 69 |
| D | 3-Isopropyl-1-methyl-cyclopentane-carboxylic acid (4-methoxy-phenyl)-amide | MS: 275, 123, 125, 69 |
| E | 3-Isopropyl-1-methyl-cyclopentane-carboxylic acid (3-cyano-phenyl)-amide | MS: 270, 153, 125, 69 |
| F | Adamantane-1-carboxylic acid (4-methoxy-phenyl)-amide | MS: 285, 135, 122 |
| G | 2-tert-Butyl-cyclopentanecarboxylic acid (4-methoxy-phenyl)-amide | MS: 275, 260, 218, 123, 69, 57 |
| H | 2-tert-Butyl-cyclohexanecarboxylic acid (2-methoxy-phenyl)-amide | MS: 289, 274, 232, 123, 108, 83, 57 |
| I | 2-tert-Butyl-cyclopentanecarboxylic acid (4-hydroxymethyl-phenyl)-amide | MS: 275, 260, 218, 123, 69, 57 |
| J | 2-tert-Butyl-cyclopentanecarboxylic acid (4-acetyl-phenyl)-amide | MS: 287, 272, 230, 153, 135, 12, 69, 57 |
| K | 2-tert-Butyl-cyclopentanecarboxylic acid (4-cyano-phenyl)-amide | MS: 270, 255, 213, 153, 125, 69, 57 |
| L | 2-tert-Butyl-cyclohexanecarboxylic acid (4-hydroxymethyl-phenyl)-amide | MS: 289, 232, 167, 123, 83, 57 |
| M | 2-tert-Butyl-cyclohexanecarboxylic acid (4-acetyl-phenyl)-amide | MS: 301, 286, 244, 139, 135, 120, 83, 57, 43 |
| N | 2-tert-Butyl-cyclohexanecarboxylic acid (4-cyano-phenyl)-amide | MS: 284, 269, 227, 167, 118, 83, 57 |

EXAMPLE 3

Application in Mouthwash

| | |
|---|---|
| Alcohol 95% | 177 mL |
| Sorbitol 70% | 250 g |
| 2-tert-Butyl-cyclohexanecarboxylic acid (4-hydroxymethyl-phenyl)-amide (1% sol. in alcohol) | 50 mL |
| Peppermint oil, Terpeneless | 0.300 g |
| Methyl salicylate | 0.640 g |
| Eucalyptol | 0.922 g |
| Thymol | 0.639 g |
| Benzoic acid | 1.500 g |
| Pluronic ® F127 | 5.000 g |
| Sodium Saccharin | 0.600 g |
| Sodium Citrate | 0.300 g |
| Citric Acid | 0.100 g |
| Water | q.s. 1 liter |

Pluronic ® F127 is a difunctional block copolymer surfactant (Trade mark of BASF)

All the ingredients are mixed. 30 mL of obtained solution is put in the mouth, swished around, gargled and spit out. A strong cooling sensation is felt in every area of the mouth.

EXAMPLE 4

Application in Toothpaste

| | |
|---|---|
| Basic opaque toothgel without flavor or fragrance | 97.0 g |
| Adamantane-1-carboxylic acid (4-methoxy-phenyl)-amide (2% sol. in PG*) | 2.5 g |
| Peppermint oil, Terpeneless | 0.5 g |

*PG = Propylene glycole

The chemicals are mixed in the toothgel, and 1 g of the toothgel is put on a toothbrush and a panelist's teeth are brushed. The mouth is rinsed with water and the water is spit out. A cooling sensation is felt by the panelist in all areas of the mouth.

The invention claimed is:

1. A compound selected from the group consisting of
   1-methyl-cyclohexane-carboxylic acid (4-cyano-phenyl)-amide,
   2-methyl-bicyclo[2.2.1]hept-5-ene-2-carboxylic acid (4-cyano-phenyl)-amide,
   3-isopropyl-1-methyl-cyclopentanecarboxylic acid (3-cyano-phenyl)-amide,
   2-tert-butyl-cyclopentanecarboxylic acid (4-hydroxymethyl-phenyl)-amide,
   2-tert-butyl-cyclopentanecarboxylic acid (4-acetyl-phenyl)-amide,
   2-tert-butyl-cyclopentanecarboxylic acid (4-cyano-phenyl)-amide,
   2-tert-butyl-cyclohexanecarboxylic acid (4-hydroxymethyl-phenyl)-amide,
   2-tert-butyl-cyclohexanecarboxylic acid (4-acetyl-phenyl)-amide and
   2-tert-butyl-cyclohexane-carboxylic acid (4-cyano-phenyl)-amide.

2. A product selected from the group consisting of topical products, oral care products, nasal care products, toilet articles, ingestible products and chewing gum, comprising a product base and an effective amount of a cooling compound selected from the group consisting of
   1-methyl-cyclohexane-carboxylic acid (4-cyano-phenyl)-amide,
   2-methyl-bicyclo[2.2.1]hept-5-ene-2-carboxylic acid (4-cyano-phenyl)-amide,
   3-isopropyl-1-methyl-cyclopentanecarboxylic acid (3-cyano-phenyl)-amide,
   2-tert-butyl-cyclopentanecarboxylic acid (4-hydroxymethyl-phenyl)-amide,
   2-tert-butyl-cyclopentanecarboxylic acid (4-acetyl-phenyl)-amide,
   2-tert-butyl-cyclopentanecarboxylic acid (4-cyano-phenyl)-amide,
   2-tert-butyl-cyclohexanecarboxylic acid (4-hydroxymethyl-phenyl)-amide,
   2-tert-butyl-cyclohexanecarboxylic acid (4-acetyl-phenyl)-amide, and
   2-tert-butyl-cyclohexane-carboxylic acid (4-cyano-phenyl)-amide.

* * * * *